US 011628028B2

(12) United States Patent
Penny et al.

(10) Patent No.: US 11,628,028 B2
(45) Date of Patent: Apr. 18, 2023

(54) ARTICULATING SURGICAL INSTRUMENT

(71) Applicant: Asensus Surgical US, Inc., Durham, NC (US)

(72) Inventors: Matthew Robert Penny, Holly Springs, NC (US); Nicholas J Jardine, Holly Springs, NC (US); Paul Wilhelm Schnur, Pipersville, PA (US); Curtis P. Hanson, Apex, NC (US); Robert Henson, Carlsbad, CA (US)

(73) Assignee: Asensus Surgical US, Inc., Durham, NC (US)

( * ) Notice: Subject to any disclaimer, the term of this patent is extended or adjusted under 35 U.S.C. 154(b) by 413 days.

(21) Appl. No.: 16/999,943

(22) Filed: Aug. 21, 2020

(65) Prior Publication Data

US 2020/0375680 A1 Dec. 3, 2020

Related U.S. Application Data

(63) Continuation-in-part of application No. 16/732,306, filed on Dec. 31, 2019.
(Continued)

(51) Int. Cl.
*A61B 34/00* (2016.01)
*A61B 34/37* (2016.01)
(Continued)

(52) U.S. Cl.
CPC .............. *A61B 34/71* (2016.02); *A61B 34/37* (2016.02); *B21D 39/00* (2013.01); *B25J 9/02* (2013.01); *B25J 9/1045* (2013.01); *B25J 9/1615* (2013.01)

(58) Field of Classification Search
CPC . A61B 34/71; A61B 34/37; A61B 2017/2937; A61B 2017/2939;
(Continued)

(56) References Cited

U.S. PATENT DOCUMENTS

| 5,792,135 A | 8/1998 | Madhani |
| 5,797,900 A | 8/1998 | Madhani |

(Continued)

FOREIGN PATENT DOCUMENTS

| EP | 2467083 B1 | 2/2015 |
| EP | 2976025 B1 | 12/2016 |

(Continued)

OTHER PUBLICATIONS

File history for commonly owned, co-pending U.S. Appl. No. 16/732,306, filed Dec. 31, 2019.
(Continued)

*Primary Examiner* — Richard G Louis

(57) ABSTRACT

A surgical instrument for use with a robotic manipulator includes an end effector assembly having one or two end effector members, each having a distal treatment end, a proximal end, and a tendon pass-through. Each end effector member is sandwiched between a corresponding pair of pulley members that, when assembled define an annular tendon pathway that is between the pulley members and that is aligned with the pass-through. For each end effector member, a tendon having a distal loop portion ends through the tendon pass-through, with its legs passing proximally from the pass-through, extending in opposite directions around the tendon pathway and proximally through the instrument's shaft.

21 Claims, 15 Drawing Sheets

Related U.S. Application Data

(60) Provisional application No. 62/787,303, filed on Jan. 1, 2019, provisional application No. 62/787,244, filed on Dec. 31, 2018.

(51) Int. Cl.
  *B25J 9/16* (2006.01)
  *B25J 9/02* (2006.01)
  *B25J 9/10* (2006.01)
  *B21D 39/00* (2006.01)

(58) Field of Classification Search
  CPC ...... A61B 2034/305; B21D 39/00; B25J 9/02; B25J 9/1045; B25J 9/1615; B25J 9/104
  See application file for complete search history.

(56) References Cited

U.S. PATENT DOCUMENTS

| | | | |
|---|---|---|---|
| 5,976,122 A | 11/1999 | Madhani | |
| 6,206,903 B1 | 3/2001 | Ramans | |
| 6,312,435 B1 | 11/2001 | Wallace | |
| 6,371,952 B1 | 4/2002 | Madhani | |
| 6,685,689 B1 | 2/2004 | Ronnberg | |
| 6,746,443 B1 | 6/2004 | Morley | |
| 6,840,938 B1 * | 1/2005 | Morley | A61B 34/71 901/29 |
| 6,902,560 B1 | 6/2005 | Morley | |
| 6,991,627 B2 | 1/2006 | Madhani | |
| 7,398,707 B2 | 7/2008 | Morley | |
| 7,621,910 B2 | 11/2009 | Sugi | |
| 7,780,651 B2 | 8/2010 | Madhani | |
| 8,241,306 B2 | 8/2012 | Grace | |
| 8,528,440 B2 | 9/2013 | Morley | |
| 8,821,480 B2 | 9/2014 | Burbank | |
| 8,852,174 B2 | 10/2014 | Burbank | |
| 9,173,643 B2 | 11/2015 | Morley | |
| 9,204,923 B2 | 12/2015 | Manzo | |
| 9,339,341 B2 | 5/2016 | Cooper | |
| 10,052,155 B2 | 8/2018 | Morley | |
| 2002/0111621 A1 | 8/2002 | Wallace | |
| 2006/0074415 A1 | 4/2006 | Scott | |
| 2009/0326530 A1 | 12/2009 | Orban, III | |
| 2010/0011900 A1 * | 1/2010 | Burbank | A61B 34/71 74/490.06 |
| 2010/0016852 A1 | 1/2010 | Manzo | |
| 2015/0209965 A1 | 7/2015 | Low | |
| 2016/0051318 A1 | 2/2016 | Manzo | |
| 2018/0116708 A1 | 5/2018 | Manzo | |
| 2018/0234814 A1 | 8/2018 | Monnes | |
| 2018/0338805 A1 | 11/2018 | Morley | |
| 2019/0090940 A1 | 3/2019 | Manzo | |

FOREIGN PATENT DOCUMENTS

| | | |
|---|---|---|
| JP | 2008161970 A | 7/2008 |
| WO | 2012043463 A1 | 4/2012 |
| WO | 2016111621 A3 | 9/2016 |
| WO | 2018234795 A1 | 12/2018 |
| WO | 2018234814 A1 | 12/2018 |

OTHER PUBLICATIONS

File history for commonly owned, co-pending U.S. Appl. No. 17/064,376, filed Oct. 6, 2020.

* cited by examiner

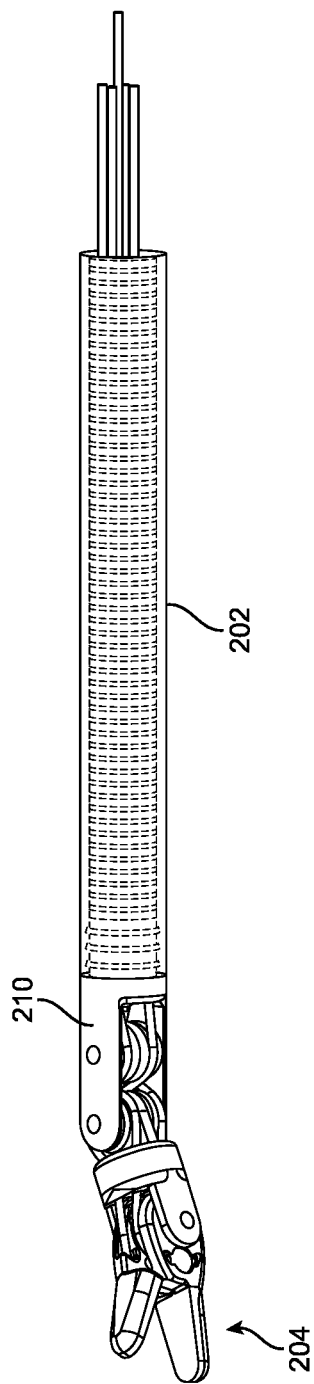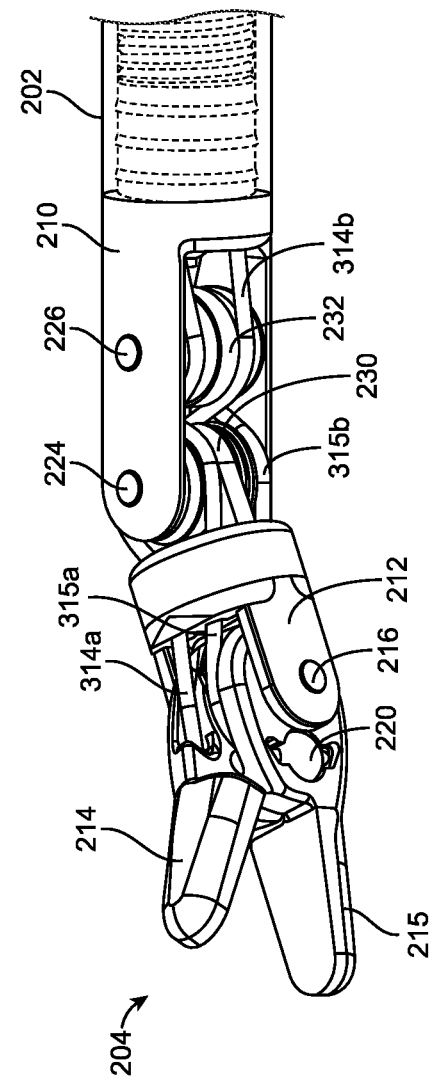
FIG. 2
FIG. 3

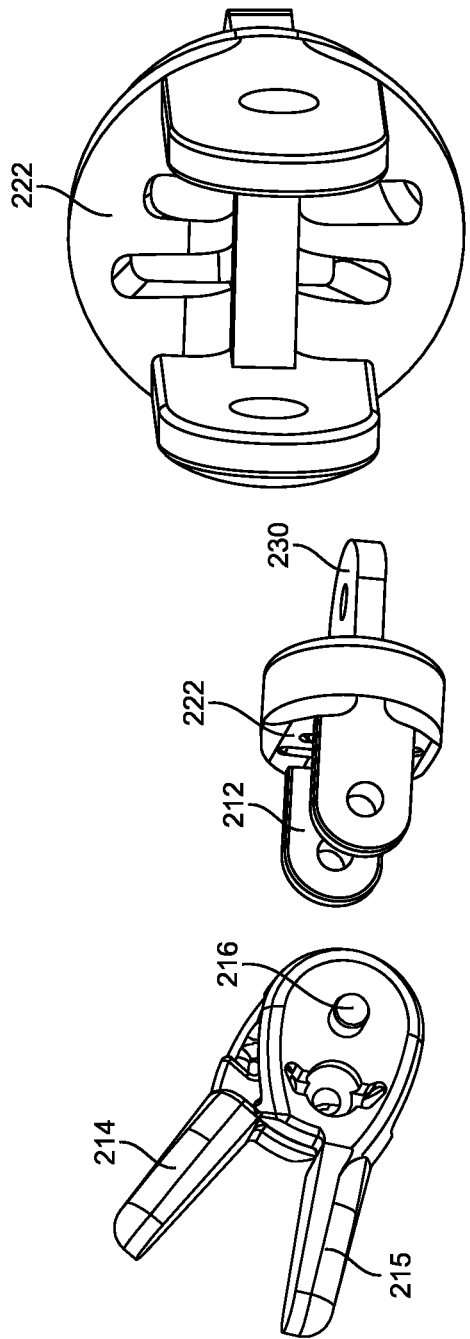
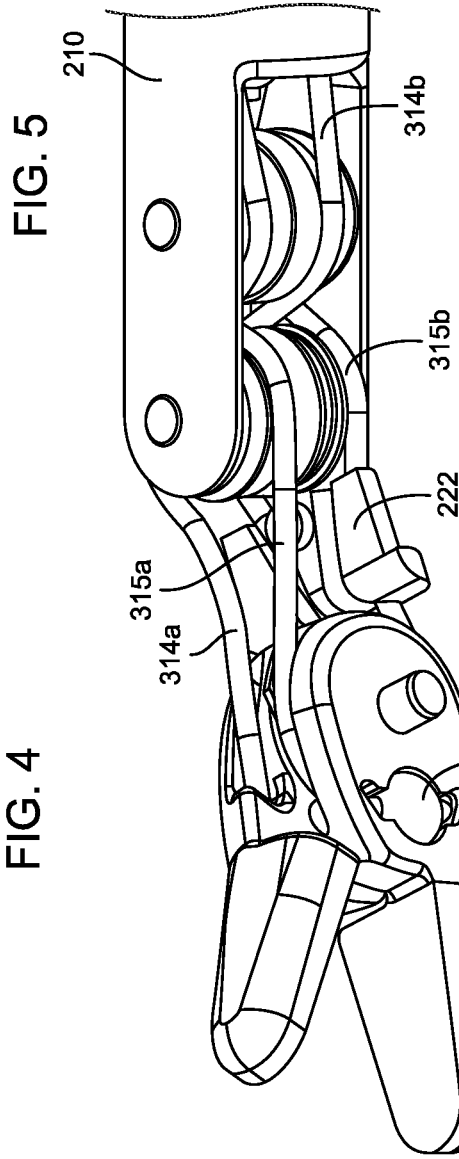

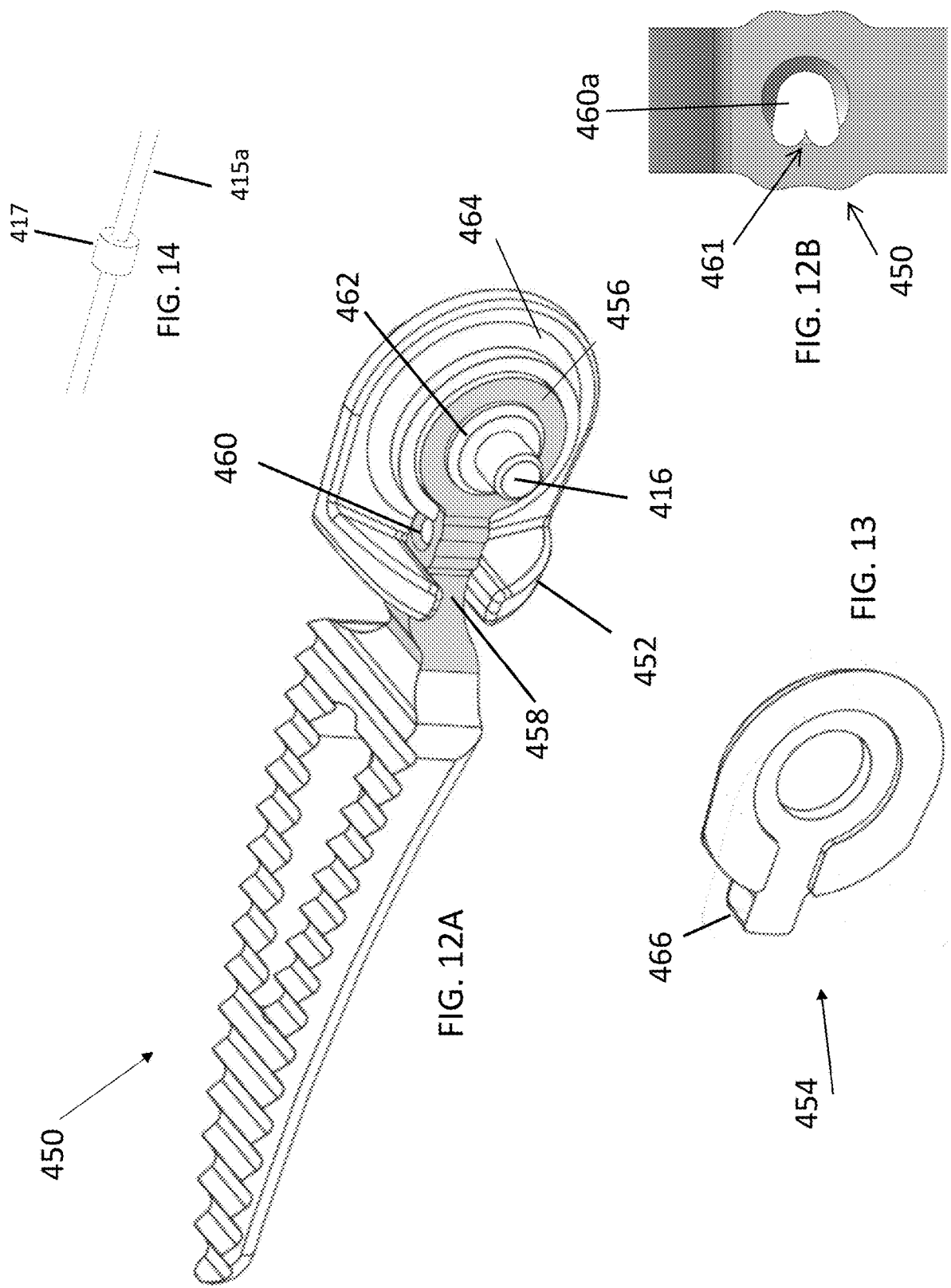

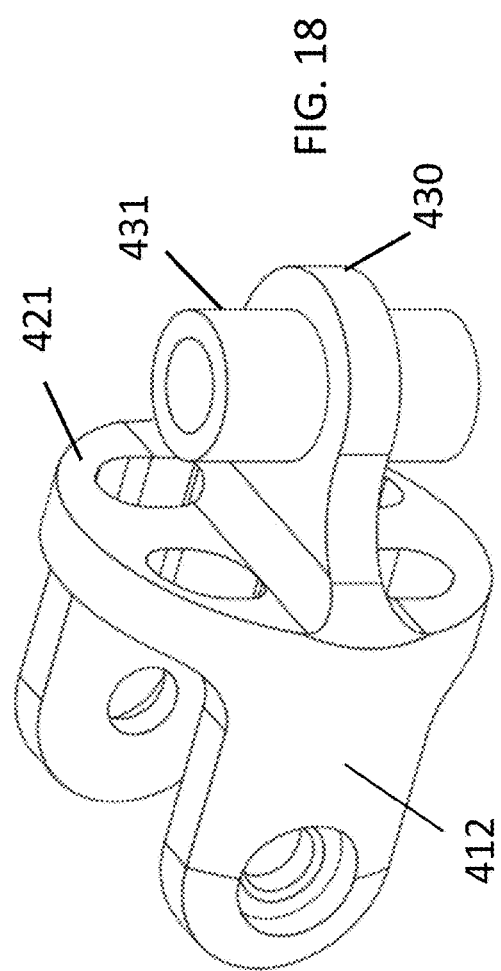
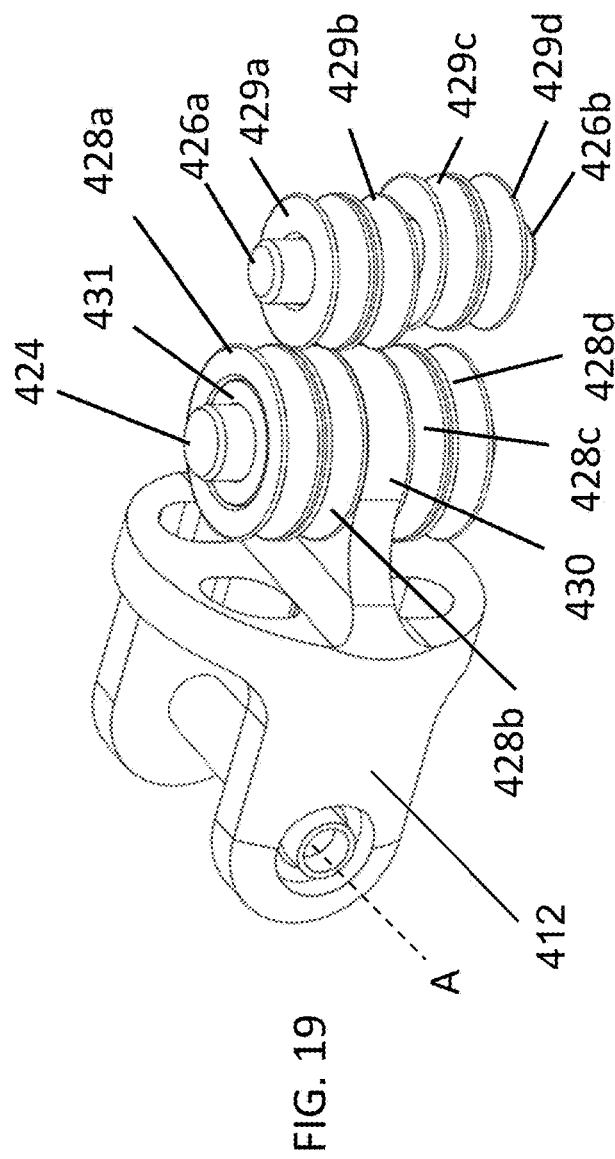

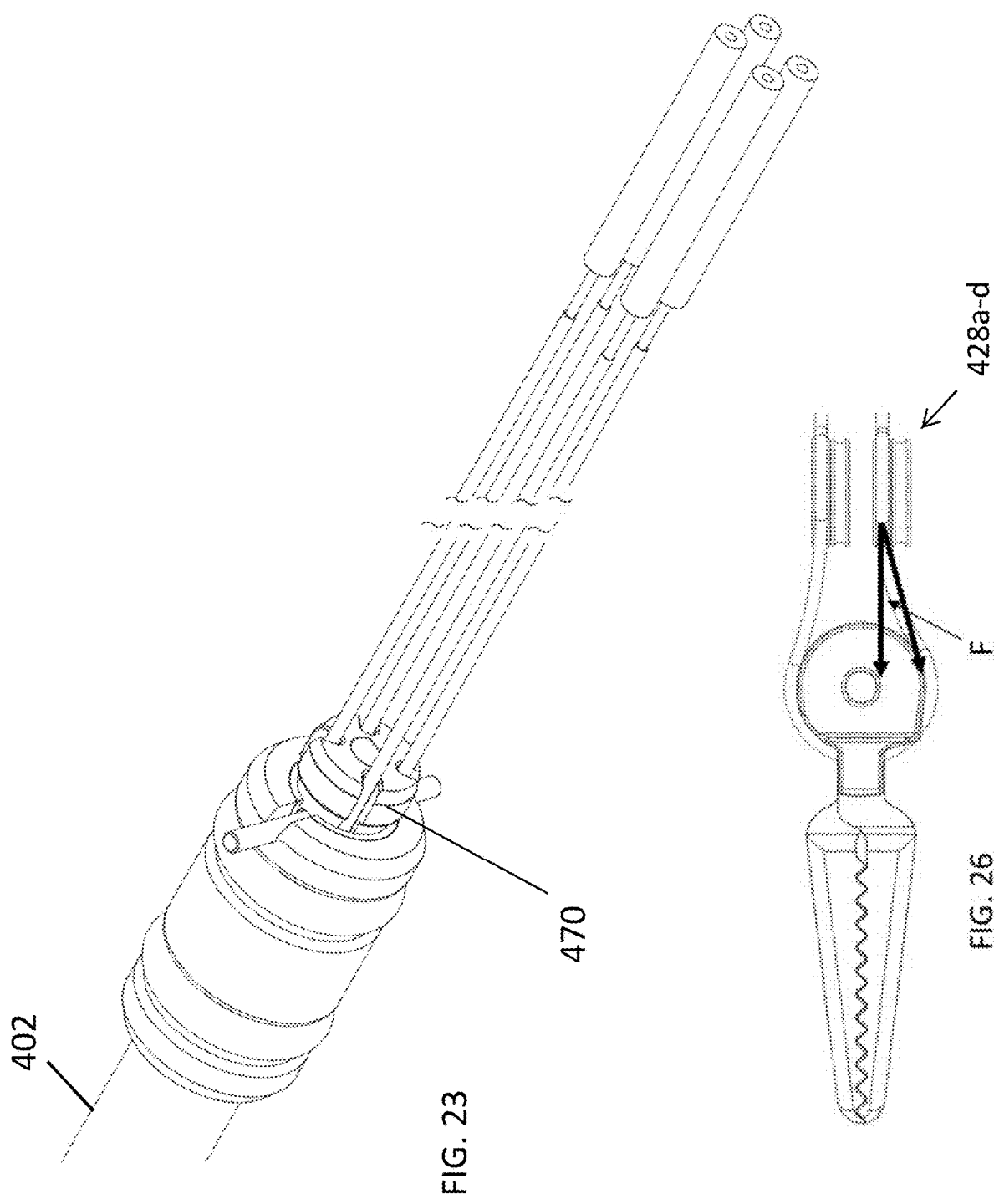

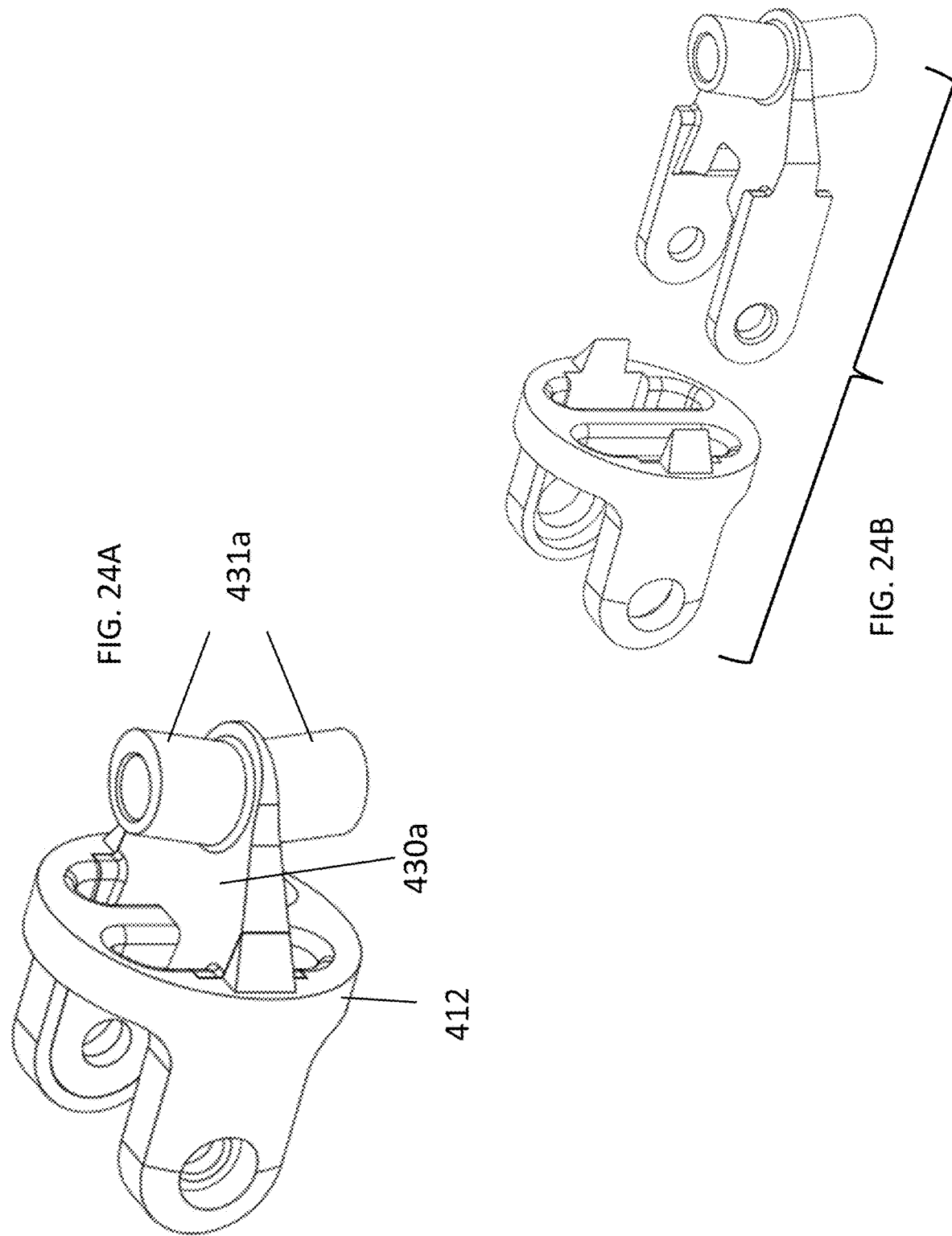

ARTICULATING SURGICAL INSTRUMENT

This application is a continuation in part of U.S. application Ser. No. 16/732,306, filed Dec. 31, 2019, which claims the benefit of U.S. Provisional Application No. 62/787,244, filed 31 Dec. 2018, and U.S. Provisional Application No. 62/787,303, filed 1 Jan. 2019.

TECHNICAL FIELD OF THE INVENTION

The present invention relates to the field of surgical devices and systems, including those using electromechanical actuation.

BACKGROUND

There are various types of surgical robotic systems on the market or under development. Some surgical robotic systems use a plurality of robotic arms. Each arm carries a surgical instrument, or the camera used to capture images from within the body for display on a monitor. See U.S. Pat. No. 9,358,682 and US 20160058513, which are incorporated herein by reference. Other surgical robotic systems use a single arm that carries a plurality of instruments and a camera that extend into the body via a single incision. Each of these types of robotic systems uses motors to position and/or orient the camera and instruments and to, where applicable, actuate the instruments. Typical configurations allow two or three instruments and the camera to be supported and manipulated by the system. Input to the system is generated based on input from a surgeon positioned at a master console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

FIG. 1A shows components of a robotic surgical system 10 of the type described in U.S. Pat. No. 9,358,682 and US 20160058513. Features of the system 10 are shown to facilitate an understanding of the way in which the concepts of the present invention may be implemented, but it should be understood that the invention may be used with a variety of different surgical or industrial robotic systems and is not limited to use with system 10.

System 10 comprises at least one robot arm 11 which operates under the control of a command console 12 operated by the surgeon, as described in the Background. The robotic manipulator (or each robotic manipulator) has a terminal portion 13 designed to support and operate a surgical device assembly 14. The surgical device assembly includes a surgical instrument having shaft 15 and a distal end effector 17 positionable within a patient 16.

In this configuration, the manipulator arm receives the surgical device assembly 14 at the terminal portion 13 as shown in FIG. 2. The surgical device assembly includes a proximal housing 20 that is received by the terminal portion 13 as shown.

The end effector 17 may be one of many different types of that are used in surgery including, without limitation, end effectors 17 having one or more of the following features: jaws that open and close, section at the distal end of the shaft that bends or articulates in one or more degrees of freedom, a tip that rolls axially relative to the shaft 15, a shaft that rolls axially relative to the manipulator arm 11. For the sake of simplicity, in FIG. 1B the end effector 17 is shown as an oval form in broken lines. The system includes instrument actuators for driving the motion of the end effector 17. These actuators, which might be motors or other types of actuators (e.g. hydraulic/pneumatic), are positioned in the terminal portion 13 of the robotic manipulator, or in the housing 20 of the surgical device assembly, or some combination of the two. In the latter example, some motion of the end effector might be driven using one or more motors in the terminal portion 13, while other motion might be driven using motors in the housing 20.

During use, the robotic system controls movement of the robotic manipulator and movement of the end effector (e.g. jaw open/close, tip roll, articulating or bending, etc.) based on surgeon input received by the system via the console 12. The control signals used to generate the various types of movement depend in some cases on the geometry, length, weight, or other parameters of the surgical instrument 14.

The system is configured to allow removal and replacement of surgical instruments 14 during the course of a procedure, so that instruments with different end effector types may be chosen as the surgeon's needs require.

Instruments that can articulate in multiple degrees of freedom can be particularly useful to a surgeon because their dexterity can simplify relatively complex tasks. Some commercially available instruments used in robotic surgery make use of three wire loops (or 6 wires) for control of the instruments degrees of freedom. A first of the loops is dedicated to one degree of freedom—the yaw motion of the instrument. A second loop controls the pitch of one jaw and the third controls the pitch of the second jaw. In the case of bipolar instruments, these instruments also run two additional cables down the instrument shaft. This brings the total number of wires/cables running the length of the shaft to 8 wires.

The described instruments are designed to minimize the overall size of the instrument shaft, as well as reducing the complexity of the assembly and part count. The instrument uses two cable loops to control pitch, yaw and jaw actuation. Some embodiments are configured to enable electrical energy to be passed through the mechanical control cables to deliver monopolar and bipolar energy to the instrument jaws.

BRIEF DESCRIPTION OF THE DRAWINGS

FIG. 2 is a perspective view of an instrument showing the shaft and distal end.

FIG. 3 is a perspective view of the distal end of the instrument.

FIG. 4 is an exploded perspective view of the jaw members and second link of the instrument.

FIG. 5 is a perspective view of the second link and associated cable guide.

FIG. 6 is a similar to FIG. 3, but the second link and a portion of the cable guide have been removed.

FIG. 12A shows the jaw member of the assembly of FIG. 11 assembled with the medial pulley section. The most proximal features of the jaw member are shown as shaded to allow easy differentiation between them and the surrounding medial pulley section.

FIG. 12B shows a portion of a slightly modified version of the jaw member of FIG. 12A, in which the pass-through has a piercing feature.

FIG. 13 is a perspective view showing the inner surface of the lateral pulley section. of the assembly FIG. 11.

FIG. 14 shows an insulated electrical cable with conductive hypotube swaged on an electrically exposed region.

FIG. 18 is a perspective view of the second link.

FIG. 19 shows the distal link assembled with the distal pulleys. The proximal pulleys and their corresponding pins are also shown.

FIG. 23 is a perspective view of the proximal end of the instrument shaft.

FIG. 24A shows an alternative second link configuration in accordance with a third embodiment.

FIG. 24B is an exploded view of the link configuration of FIG. 24A.

FIG. 26 shows a side view of jaw members, distal pulleys, and a tendon and illustrates a fleet angle of the tendon.

DETAILED DESCRIPTION

First Embodiment

Figure 1A:
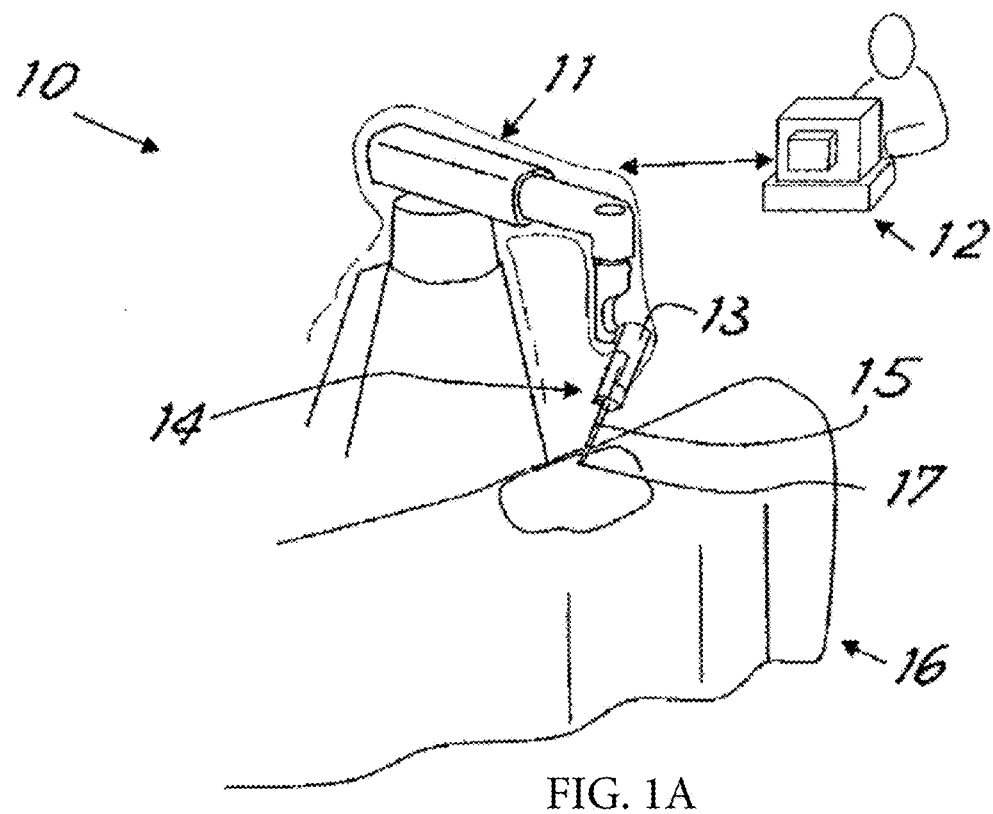
FIG. 1A schematically illustrates a robotic manipulator of a type used in robotic surgical procedures.
Figure 1B:
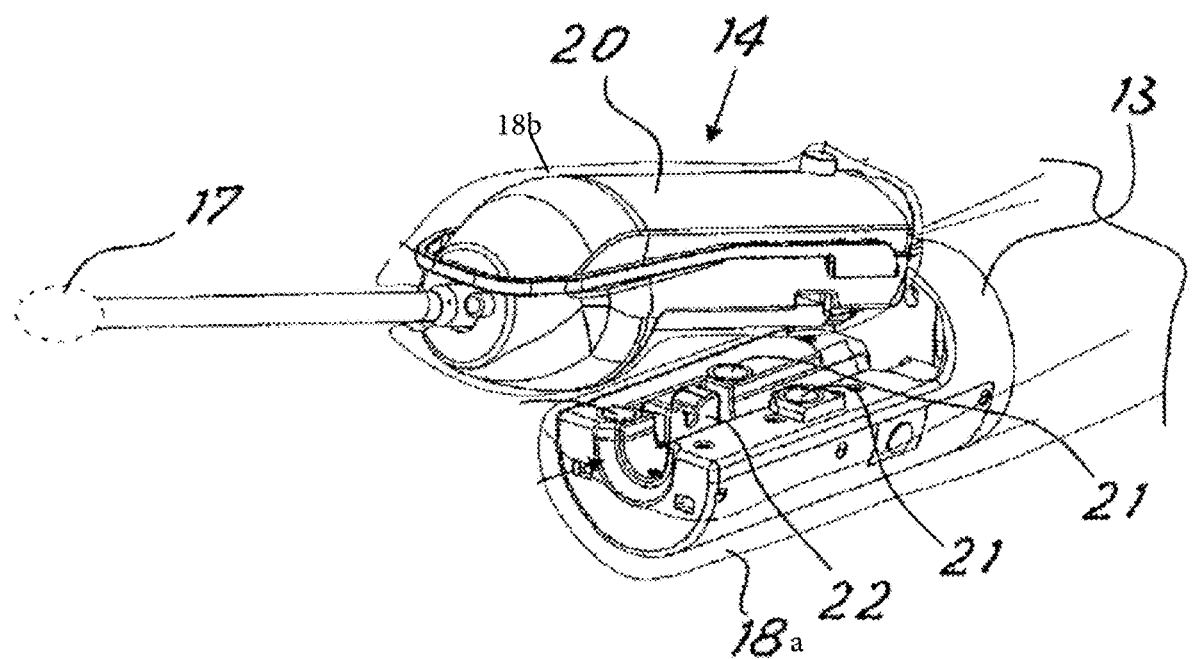
FIG. 1B illustrates the step of mounting of a surgical device onto the manipulator of FIG. 1A.

Details of a first embodiment of an instrument 200 will next be described with reference to FIGS. 2 through 9.

Referring to FIGS. 2 and 3, the distal end of the instrument 200 includes a first link 210 mounted on the distal end of the shaft 202. A second link 212 is coupled by a pin 224 to the first link 210, allowing the second link to pivot relative to the first link. Each of the links 210, 212 is preferably a clevis type of link. A pair of jaw members 214, 215 are coupled to the second link 212 by a pin 216 (e.g. at a distally extending member of clevis link 212 as is shown) such that the jaw members 214, 215 can independently pivot about the pin 216 relative to the second link 212.

Four drive cables extend through the shaft 202 and links 210, 212 to the end effector: first cables 314a, 314b, which terminate at jaw member 214, and second cables 315a, 315b that terminate at jaw member 215. In this description, cables 314a, 315a may be referred to as "upper cables" and cables 314b, 315b may be referred to as "lower cables". All orientation references such as these are used for the sake of convenience in describing the orientation of these features in the drawings, and should not be construed to require a particular orientation for the end effector etc.

Figure 7:
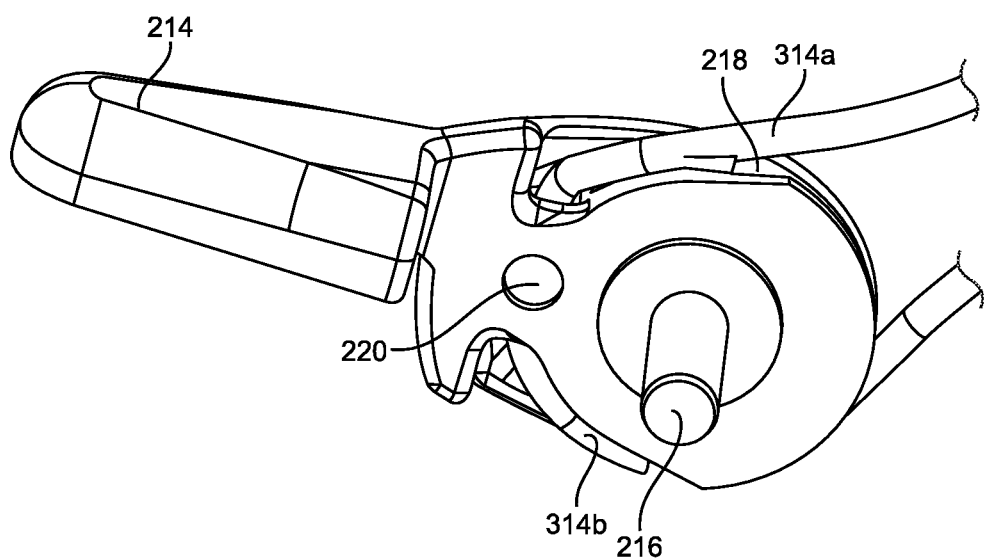
FIG. 7 is a perspective view of one jaw member and its corresponding cables.

Each jaw member may include cable guide features around which the cables are routed. In the jaw members shown in the drawings of the first embodiment, the proximal portion of the jaw member is shaped similar to a pulley, with a partially-annular groove 218 having a profile that curves with a constant radius relative to the axis of the pin 216. The groove 218 for jaw member 214 is shown in FIG. 7. As shown, the upper cable 314a and the lower cable 314b pass along the groove in opposite directions, meeting at a common anchor point. In this embodiment, the distal end of each cable 314a, 314b is secured to a common ball crimp 220 that is secured within a recess in the jaw member 214. It should be mentioned that in this and the subsequent embodiments, each of the cables 314a, 314b may be a single cable, with crimp 220 only used to secure the cable to the jaw member (and, in some embodiments, to provide electrical conduction to the jaws, as discussed below), or it may be two cables crimped together by crimp 220.

Referring again to FIGS. 4-5, additional cable guides 222 for the upper and lower cables are housed within the second link 212. In FIG. 6, the second link 212 is not shown and only the lower cable guides 222 are shown, so as to allow the path of the lower cables 314b, 315b through the cable guide 222 to be seen.

Figure 8:
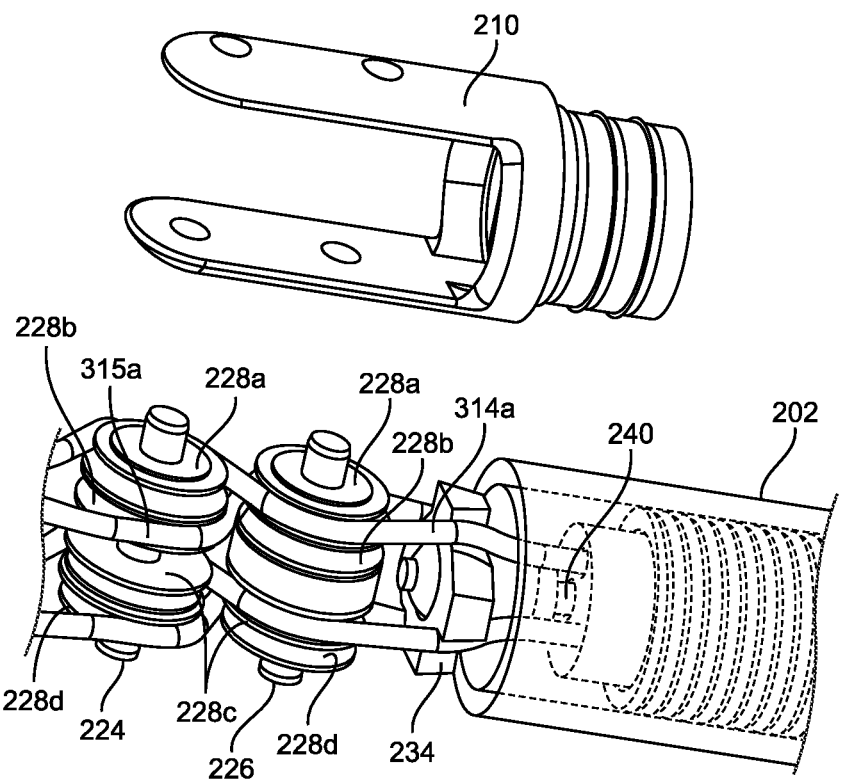
FIG. 8 is an exploded perspective view of the first link and its contents.

From the cable guides 222, the cables extend proximally into the first link 210, which may be a clevis-type link as shown. FIG. 8 gives a partially exploded view of the first link 210 so its contents can be seen. Within the first link 210 is a pair of parallel pins 224, 226. Each of these pins has four cable pulleys 228 a-d rotatably positioned on it as shown. Each of the cables 314a, 314b, 315a, 315b extends in a first direction around one of the pulleys and then in the opposite direction around the co-axially adjacent pulley. In the drawings, upper cable 314a extends around pulleys 228a, upper cable 315a extends around pulleys 228b. The lower cables 314b, 315a extend around lower pulleys 228c and 228d, respectively. As best shown in FIG. 3, proximally-extending tongue 230 of second link 212 is positioned on the pin 224, between pulleys 228a and 228c, to allow the second link 212 to pivot about the pin 224 relative to the first link 210. A washer 232 is disposed between pulleys 228a and 228c on the second pin 226, allowing the pulleys on the pins 224 to remain aligned with their counterparts on pin 226.

Referring again to FIG. 8, the cables pass proximally from the first link 210 into the instrument shaft 202. To maintain orientation and alignment of the cables, they may pass over or through an additional cable guide as they enter into the instrument shaft 202. One such cable guide 234 is shown in FIG. 8.

The proximal ends of the drive cables 314a-b, 315a-b are engaged with actuators that may be disposed in a housing at the proximal end of the shaft 202. These actuators are driven by or receive mechanical input from drive motors disposed within a component of the robotic surgical system that receives the instrument, such as the terminal portion of the robotic arm. One configuration is shown in commonly owned co-pending application Ser. No. 16/732,307, entitled Compact Actuation Configuration and Expandable Instrument Receiver for Robotically Controlled Surgical Instruments, filed Dec. 31, 2019, which is incorporated herein by reference. The actuators may be configured to receive linear and/or rotational drive input to selectively alter the tension on the drive cables, resulting in movement of the jaws and/or link 212.

Given the arrangement of cables at the end effector, movement in accordance with the following degrees of freedom can be achieved using combination of tension in the respective cables listed on Table 1 below. Note that in the table, "+" means tension is applied to, or increased in, the cable, and "−" means tension is reduced or released. The indications of "up", "down" are relative to the page of the figures. The indications of "left" and "right" are assuming the user is looking distally down the shaft of the instrument towards the end effector.

TABLE 1

| Movement | Cables for Jaw Member 214 | | Cables for Jaw Member 214 | | Pivot Axis |
|---|---|---|---|---|---|
| | Cable 314a (upper) | Cable 314b (lower) | Cable 315a (upper) | Cable 315b (lower) | |
| Pitch Up | + | − | + | − | Pin 216 |
| Pitch Down | − | + | − | + | Pin 216 |
| Yaw Left | − | − | + | + | Pin 224 |
| Yaw Right | + | + | − | − | Pin 224 |
| Jaw Open | + | − | − | + | Pin 216 |
| Jaw Close | − | + | + | − | Pin 216 |

An additional degree of freedom of the end effector is that of that axial rolling, which is achieved by rotating the shaft 202 about its axis.

As indicated in Table 1, yaw motion of the end effector in one direction or the other involves simultaneously tensioning both cables associated with one jaw member and simultaneously relaxing both cables associated with the other jaw member. Pitch motion is achieved by pivoting both jaws in the same direction (up or down) about pin 216. As shown in Table 1, upward pitch results when both upper cables 314a, 315a are tensioned while both lower cables 314b, 315b are relaxed, and downward pitch occurs when the lower cables are tensioned and the upper cables are relaxed. The jaws are closed, such as for grasping, by pivoting jaw members 214, 215 towards one another about pin 216. As shown on Table 1, to close the jaws, lower cable 314b of jaw member 214 and upper cable 315a of jaw member 215 are tensioned. To open the jaws, upper cable 314a of jaw member 214 and lower cable 315b of jaw member 215 are tensioned.

The cables may be stainless steel braided cables, tungsten braided cables, or any other tendon, wire or cable having the appropriate strength, durability and other properties for its intended use. Note that in this description the terms "tendon," "wire," and "cable" are used broadly to encompass any type of tendon that can be used for the described purpose.

Figure 9:
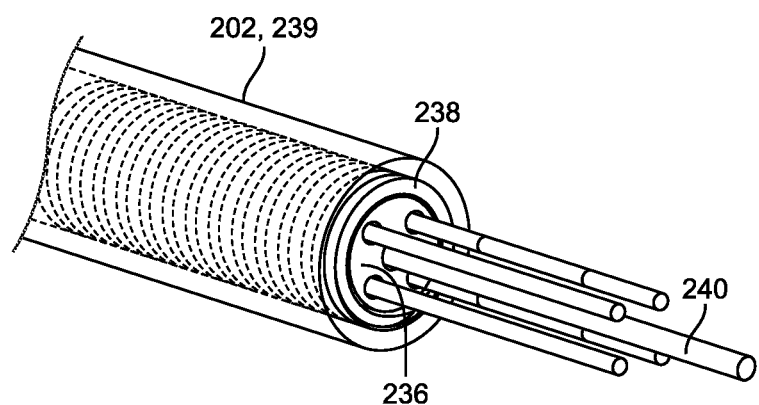
FIG. 9 is a perspective view of the proximal end of the instrument shaft, showing the drive cables and stiffening cable.
Figure 10:
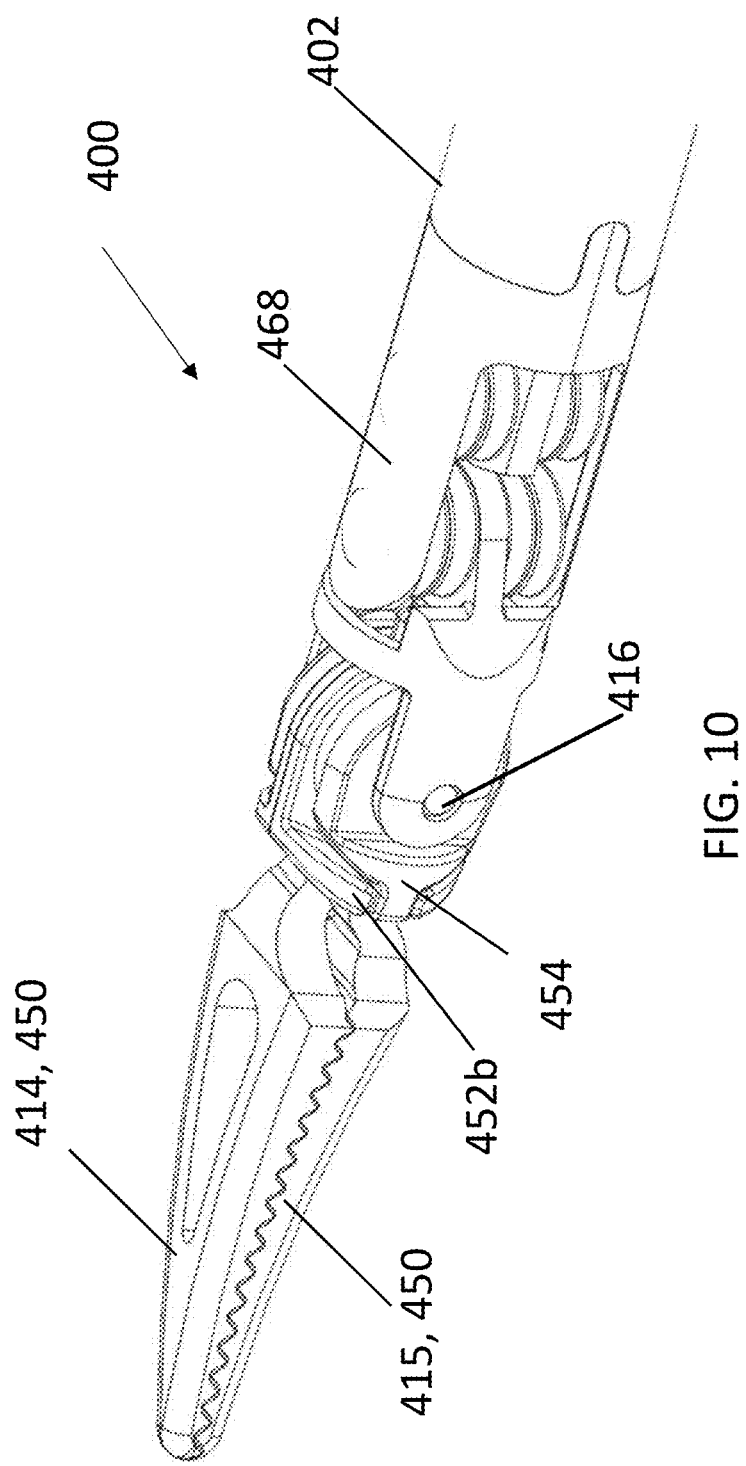
FIG. 10 is a perspective view of a second embodiment of an instrument.

The shaft 202 may be rigid, as may be suitable for use with the systems described in the Background, or it may include an elongate flexible section so that it may be used through flexible (e.g. steerable) cannulas. FIG. 9 shows one example of a flexible shaft design, which includes an inner member 236 having multiple lumen for accommodating the drive cables. A coil pipe 238 is disposed over the inner member 236, and an outer layer 239 former of braided Pebax or other suitable material covers the coil pipe 238. Inner member 236 may include four lumen for the four drive cables 314a-b, 315a-b, as shown, plus a central lumen housing an additional stiffening cable 240. Cable 240 has a distal end terminating at the distal end of the shaft such that tensioning the cable compresses the windings of the coil pipe 238, increasing its rigidity. Referring to FIG. 8, in the drawings the cable 240 is anchored by a ball crimp to the cable guide 234 positioned within the first link 210. The system may be configured to apply tension to the cable in one of several ways, e.g. the tension may be continuously applied, or it might be dynamically applied by a motor during use of the system.

Second Embodiment

FIGS. 10-23 show a second embodiment of an instrument 400, which is suitable for electrosurgical instruments in which electrical energy is conducted to one or both jaw members for delivery to body tissue, but which has features that may be used for non-electrosurgical instruments as well. It shares many common features with the first embodiment. Those that differ will be discussed here. Although a Maryland dissector end effector is shown, the instrument may be manufactured using any jaw configuration useful in surgery, including graspers, scissors, and needle holders, or other end effectors for which pitch and yaw motion is useful but there are no jaws to actuate. For example, the instrument may be manufactured with a single "jaw" that does not open and close, but is steerable in pitch and yaw. Examples of these configurations include monopolar hooks, monopolar spatulas, and suction/irrigation devices.

Figure 11:
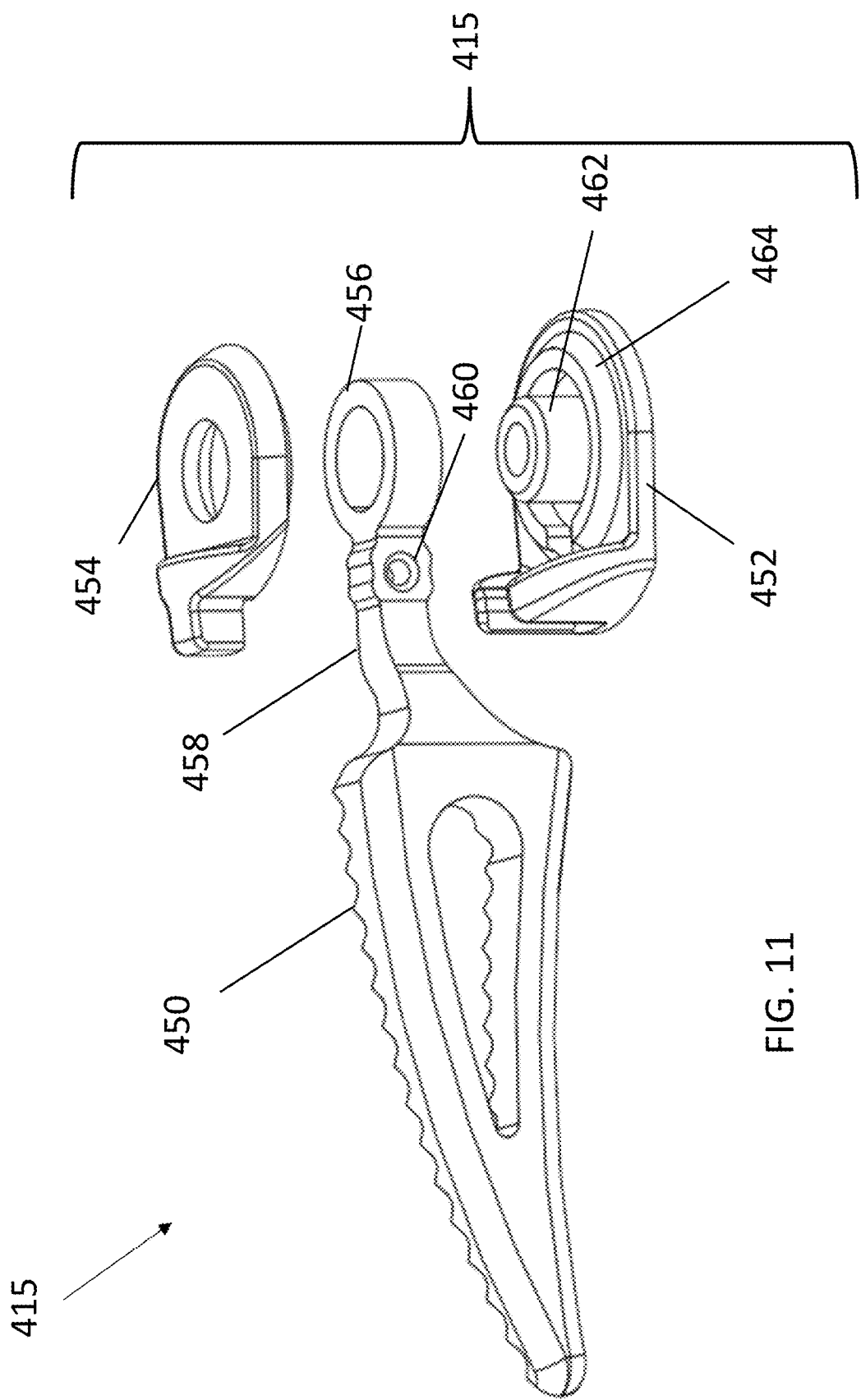
FIG. 11 is an exploded perspective view of a jaw member assembly of the instrument of FIG. 10.

The end effector of the instrument 400 has a pair of jaw member assemblies 414, 415. An exploded view of one of jaw member assemblies 415 of the second embodiment is shown in FIG. 11; the other 414 has identical features except for differences between the jaw members themselves that may be dictated by the type of surgical instrument. Each jaw member assembly includes a jaw member 450, medial pulley section 452, and a lateral pulley section 454. Jaw member 450 has a collar 456 connected to the jaw by a proximally-extending stem 458. A pass-through 460 in the stem 458 receives the cable (not shown, but see FIG. 15) for mechanical actuation of the jaw member 450 and, optionally, for conduction of electrical energy to the jaw member 450.

When the jaw member assembly 415 is assembled, the collar 456 of the jaw member 450 is captured between the medial and lateral pulley sections 452, 454. One of the pulley sections may include an annular post 462 to help retain the jaw member 450 between the pulley section. In this embodiment, the lumen of the collar 456 of the jaw member 450 is disposed over the annular post 462. See FIG. 12A. When the end effector is fully assembled, pin 416 (which is the pin about which the jaw members pivot for open-close and pitch motion) extends through the lumen of the posts 462 of each of the jaw member assemblies. See FIGS. 12A and 16.

Figure 15:
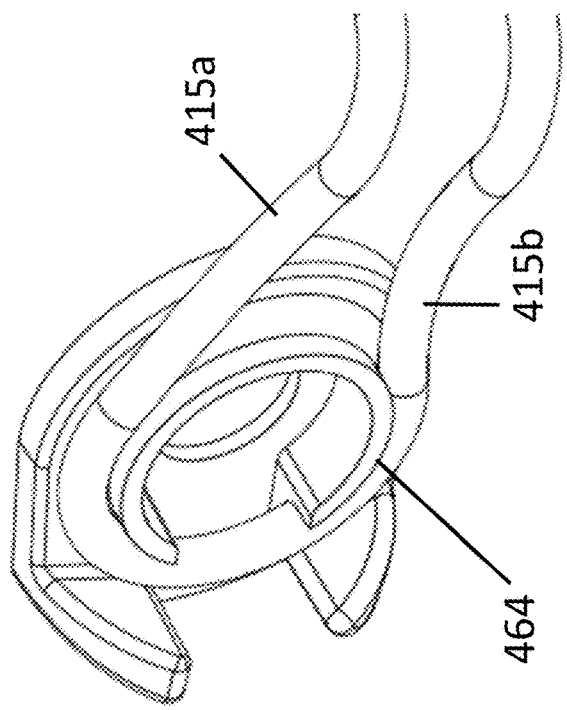
FIG. 15 shows the medial pulley of the assembly of FIG. 11 with a cable positioned on it.
Figure 16:
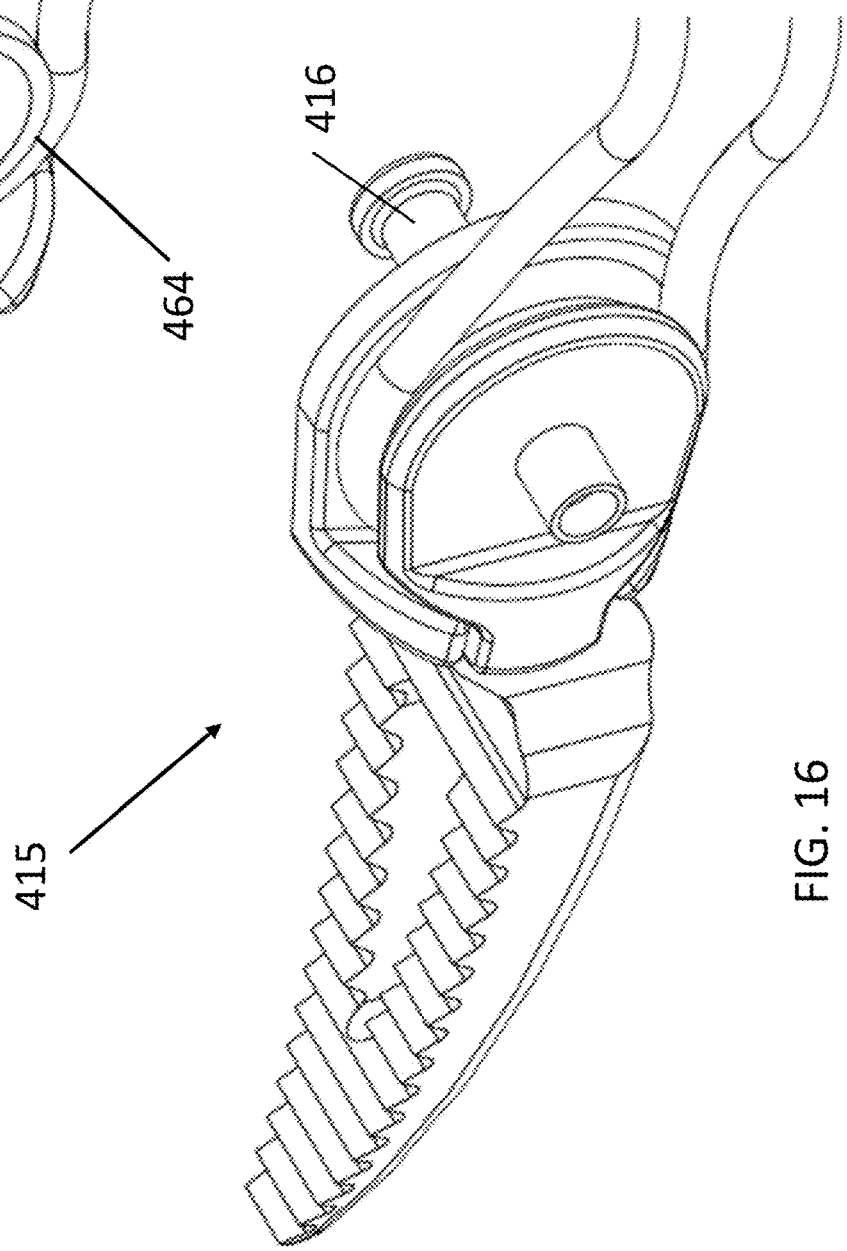
FIG. 16 shows the jaw member assembly of FIG. 11 assembled with a cable.

The medial and lateral pulley sections have opposed faces possessing surface geometry that, when they are assembled, define an annular pathway through which the cable is routed. In the illustrated embodiment, an annular rib 464 on one of these pulley sections (shown on the medical section but it may be on either) may contact the opposed face of the other of the pulley sections to define the pathway. As will be understood from viewing FIG. 12A, the cable pathway defined by annular rib 464 is aligned with the pass-through 460 (in the stem 458) from which the cable extends. In this drawing, the most proximal features of the jaw member 350 are shown as shaded so those features may be easily differentiated from those of the medial pulley section. The lateral pulley section is hidden in this view to allow these features to be seen, but its face that opposes the medial pulley section is shown in FIG. 13. The cable 415a, 415b routes around the annular rib 464 as shown in FIGS. 15 and 16 and is captured within the jaw member assembly by the contact between the edges of the rib 464 and the opposed face of the lateral pulley section 454. It should be understood that the geometry of the medial and lateral pulley sections' opposed faces may have any configuration that forms an annular pathway for routing of the cable. Examples include various combinations of annular ribs and/or channels, and recesses and/or faces.

The three primary elements of the jaw member assembly may be keyed or mated together to ensure rotation as a unit during use. Referring to again to FIGS. 12A and 13, as one non-limiting example, a distal face of the medial pulley section 452 includes a lateral slot that receives the stem 458 of the jaw member 450 and a tab 466 of the lateral pulley section 454.

Where the jaw assembly is used for electrosurgical applications, the jaw member 450 is formed of a conductive material, while the medial and lateral pulley sections are formed of insulating materials.

A particular advantage of the disclosed jaw assembly is that it allows a variety of articulating instrument types (e.g. Maryland grasper, needle holder, scissors) to be assembled from sets of components that are identical to one another except for the jaw member 450 itself. In other words, the component parts can be manufactured so that each instrument type can utilize identical medial and lateral pulley sections, but different jaw members 450 having the appropriate jaw shapes.

For electrosurgical instruments, the second embodiment provides the advantages of delivering both mechanical and electrical energy with the same cables, which reduces the number of cables needed for the instrument. This also allows the use of larger cables (for increased strength), or a reduction in the diameter of the instrument shaft than might be achieved using separate electrical and mechanical cables.

Methods and configurations for electrically and mechanically connecting the cables to the jaw members will next be described. The purpose of these concepts is to achieve a mechanical bond between jaw and cable capable of delivering adequate jaw grasping and spreading strength as well as to achieve an electrical bond between jaw and cable capable of reliably delivering electrocautery to the surgical site. These two requirements must be achieved in such a way that the rest of the instrument remains isolated from the electricity passing through the cable to the jaw to prevent undesired tissue damage.

According to a first method, each cable (see cable 415s in FIGS. 14 and 15) used for mechanical and electrical energy delivery is a cable covered or coated with an insulative material, such as an extrusion-coated conductive cable. The coating on the cable is selectively stripped at a location where the jaw is to be crimped in place. For example, where a single wire loop is used through each jaw, insulation is locally removed from the approximate mid-point or the middle region of the cable to create an exposed region. The ends of the cables can also be stripped, and with a service loop long enough to compensate for cable travel, the ends can be attached to the external energy connectors. The removal process could be performed manually with a blade or wire stripping tool or through a more automated processes including, but not limited to, laser ablation, etching, localized melting, etc.

The cable is assembled with the relevant electrically conductive jaw member with the exposed conductive region positioned in electrical contact with the jaw member. When a jaw member of the type used for the FIG. 12A embodiment is used, the cable passes through pass-through 460 such that the exposed region of the cable is within the pass-through. This is the location at which the coated cable is engaged with the end effector jaw for both jaw movement and electrical conduction. The pass-through 460 is large enough for the coated cable to pass through, but small enough to engage with the uncoated section of cable when crimped in the assembly process. In a preferred embodiment illustrated in FIG. 14, a section of electrically conductive hypotube 417 is swaged to the cable 415a to fill the area of removed insulation with an electrically conductive material. The swaged hypotube 417 is then fed into the pass-through 460. Once the jaw is crimped to the cable loop, it is electrically coupled with the cable, while the remaining length of the cable remains insulated.

In a slight modification to this embodiment, the hypotube 417 may be coupled to the jaw prior to crimping. For example it might be positioned in the pass-through such as by being welded or otherwise attached to the jaw or seated in a pocket positioned on the jaw.

In an alternative method, the cable is one coated with a dielectric polymer. The jaw is formed with a cable pass-through 460a having a geometry designed such that compression of the pass-through during crimping will pierce the dielectric polymer coating on the cable, creating the electrical connection between cable and jaw. At the same time, the compression of the pass-through creates the mechanical bond between cable and jaw. Referring to FIG. 12B, the geometry of the pass-through 460a may, for example, include a sharp member 461 that extends into the pass-through, with "sharp" intended to mean that it is sufficiently sharp to penetrate the polymer coating during crimping. As one specific example, the member may extend radially inwardly and include a sharpened edge oriented parallel to the axis of the pass-through. In other examples, the sharp member will have different shapes and orientations.

A third method also uses a length of cable coated with a dielectric polymer. In this method, the section of the cable that is to be crimped to the jaw member is identified and the coating in that section is removed prior to crimping the jaw to the cable. Once the segment of coating has been removed, the cable may be inserted through the pass through in the jaw such that the jaw is aligned with the uncoated segment. Once aligned, the jaw is crimped and the compression of the pass through creates the electrical and mechanical connection to the cable beneath the dielectric coating.

A fourth method makes use of a length of cable that is not coated with a dielectric polymer. It is fed through pass-through 460 in the jaw member. The pass-through is compressed in a crimping operation to create the mechanical and electrical connection between cable and jaw. Dielectric material is applied over each portion of the cable extending away from the pass-through, providing electrical isolation along the length of the cable that is outside the pass-through. This dielectric material may be heat shrink tubing or some other tubing applied on the cable, or it might be a dipped or sprayed dielectric coating. If heat shrink tubing is used, the cable will be fed into the tube and the tube shrunk down onto the cable to form a physical barrier between the cable and the rest of the instrument assembly.

A fifth method makes use of two separate cables to form the cable coupled to a jaw. In this configuration, the end of each cable is stripped of the dielectric polymer coating. The stripped ends of both cables are positioned in the pass-through 460 in the jaw member and the pass-through is then compressed in a crimping operation.

Features unique to this invention include the use of a shaped pass through designed to pierce a dielectric coating on a wire during the fabrication of a surgical instrument, and the application of heat shrink tubing to either side of an uncoated cable, after that cable has been crimped to a surgical instrument jaw.

In each embodiment, because the cable is pulled through a series of pulleys and conductive structures for steering the instrument end effector, the insulative coating is sufficiently thick and durable to prevent electrical energy conducted through the cable from passing to components of the instrument that are not intended to be energized.

When both jaws have been crimped to the middle of each coated cable, the assembly of the joints of the instrument can begin. The coated cables are threaded through the pulley structure and down the instrument shaft to the cable control geometry. The exposed free ends of each cable loop are attached to an electrical connector to which a line from an electrosurgical generator unit may be coupled in the operating room. In preferred configurations, there is a service loop between the electrical connector and the actuation mechanism that is configured to engage with the robotic manipulator. The service loop allows the actuation mechanism to progress through its range of motion without imparting stress to the section of cable that is attached to the electrical connector.

Figure 17:
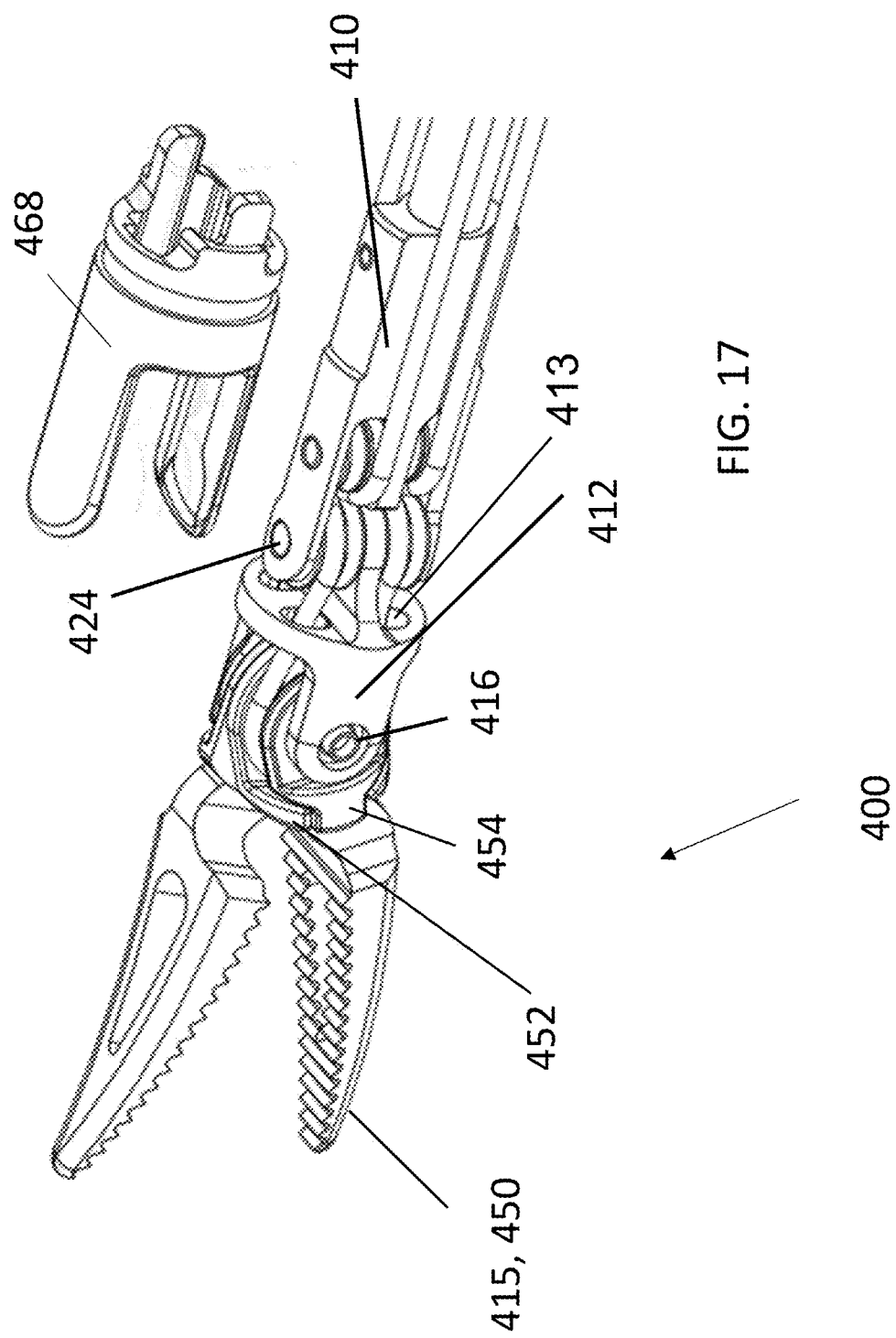
FIG. 17 is similar to FIG. 10, but shows the clevis cover removed from the first link.
Figure 22:
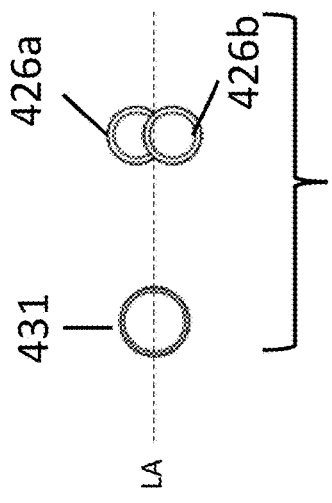
FIG. 22 is a plan view of the boss and the pins for the proximal pulleys.
Figure 20:
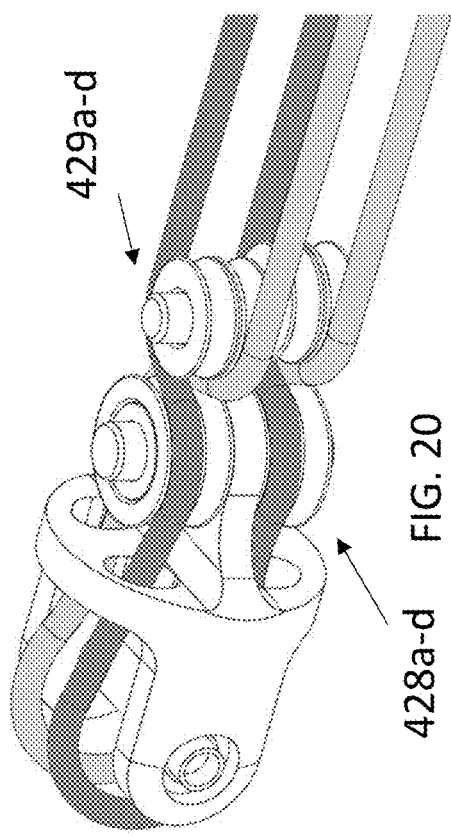
FIG. 20 is similar to FIG. 19 but also shows the cables. For clarity, one cable is lightly shaded and the other cable is more darkly shaded.

Referring to FIG. 17, the first and second links 410, 412 of the second embodiment perform similar functions to the first and second links 210, 212 of the first embodiment. The pin 416 couples each of the lateral and medial pulley sections 452, 454 and each of the jaw member assemblies 414, 415 to the second link 412 at its distally-extending clevis. A transverse face 421 of the second link 412 includes wire guide openings 413 for the four cable segments 414a,b and 415a,b. See also FIG. 18. A tongue 430 (FIG. 18) extends proximally from the face 421. Bosses 431 extend from opposite sides or faces of the tongue. As shown in FIG. 19, rather than rotating on a pin, the distal pulleys 428a-d rotate on these bosses 431, with upper pulleys 428a, 428b on the upper boss 431, and lower pulleys 428c, 428d on the lower boss (not visible in FIG. 19). This helps to prevent the link 412 from binding the pulleys due to tilting or sliding along its pivot axis A, which can occur in response to load changes on the cables. A pin 424 extends through the bosses 431. This pin is used to couple the second link 412 and distal pulleys 428a-d to the first link 410, as shown in FIG. 17.

The wire guide openings 413 may be defined by a single integral component, or they may be defined by a combination of more than one component, depending on the desired material properties of the guiding surfaces.

Figure 21:
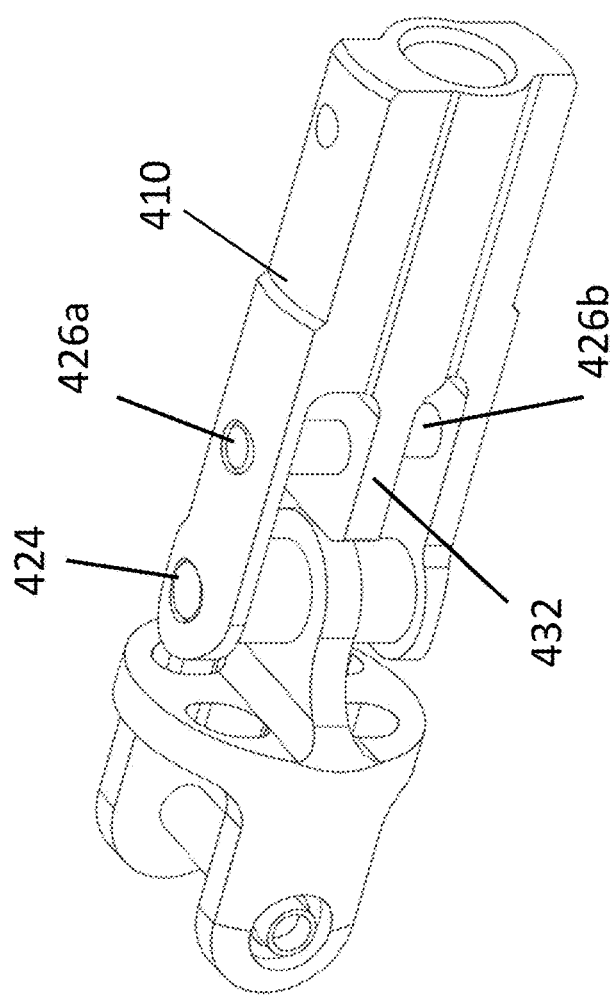
FIG. 21 shows the first link assembled to the second link.

FIG. 21 shows the first link 410 assembled with the second link 412. A tab 432 extends between and in parallel to the link's longitudinally-extending clevis arms. A first pin 426a extends between the upper clevis arm and the tab 432, and a second pin 426b extends between the tab 432 and the lower clevis arm. Proximal pulleys 429a-d rotate on these pins, with two pulleys 429a-b on one side of the tab 432 and two pulleys 429c-d on the other side of the tab. Separating these pulleys allows the pulleys on the bosses 431 to remain aligned with their counterparts on pins 426. Referring to the plan view of the bosses 431 and pins 426a,b shown in FIG. 22, pins 426a,b preferably do not share a common axis. In the illustrated embodiment, the axes are laterally offset from one another and from the longitudinal axis LA of the instrument. On the other hand, the bosses 431 have axes that intersect the longitudinal axis LA of the instrument. In alternative embodiments, the pins 426a,b may be axially aligned, or they might even comprise a single pin extending from the upper clevis arm, through an opening in the tab 432, to the lower clevis arm.

Arranging the upper proximal pulley stack to have an axis that is offset from the axis of the lower proximal pulley stack standardizes the locations at which the cables exit the end effector, standardizes the cable exit locations and standardizes the impact of cable force to shaft deflection by making sure the cables are all the same distance from the shaft central axis and minimizes the likelihood that the cables routed around the pulleys will rub against internal edges in the instrument shaft.

Referring again to FIG. 10, a clevis cover 468 (see also FIG. 17) covers a portion of the link 410. The clevis cover is an insulating plastic part that helps to guide the cables to their intended locations in the shaft. The link 410 extends proximally into the instrument shaft 402, which is preferably a rigid shaft. The proximal end of the shaft 402 is shown in FIG. 23, which shows that the cables exit the shaft 402 via a seal 470 that includes passages for each of the cables. This seal functions as an assembly tool during the assembly process, by helping align the cables. During the final stages of assembly, it is compressed to create one or more seals against the adjacent shaft and end cap components. During use of the instrument in surgery, the seals helps to prevent loss of pneumoperitoneum through leakage of gas through instrument shaft.

The proximal ends of the drive cables are engaged with actuators that may be disposed in a housing supported at the proximal end of the shaft 402. These actuators are driven by or receive mechanical input from drive motors disposed within a component of the robotic surgical system that receives the instrument, such as the terminal portion of the robotic arm. One configuration is shown in commonly owned co-pending application Ser. No. 16/732,307, filed Dec. 31, 2019, entitled Compact Actuation Configuration and Expandable Instrument Receiver for Robotically Controlled Surgical Instruments, which is incorporated herein by reference. The actuators may be configured to receive linear and/or rotational drive input to selectively alter the tension on the drive cables, resulting in movement of the jaws and/or link 412.

In use, actuation of the cables in the manner described with respect to the first embodiment produces the types of motion (pitch, yaw and jaw open-close) delineated in that description, and reference should be made to that discussion for details pertaining to those types of motion. As with that embodiment, pitch motion and jaw open-close motion occurs about the axis of pin 416 that extends through the pulleys defined by the lateral and medial pulley sections of each jaw member assembly. Yaw motion occurs about the axis of the pin 428 extending through distal pulleys 428a-d.

Third Embodiment

Figure 25:
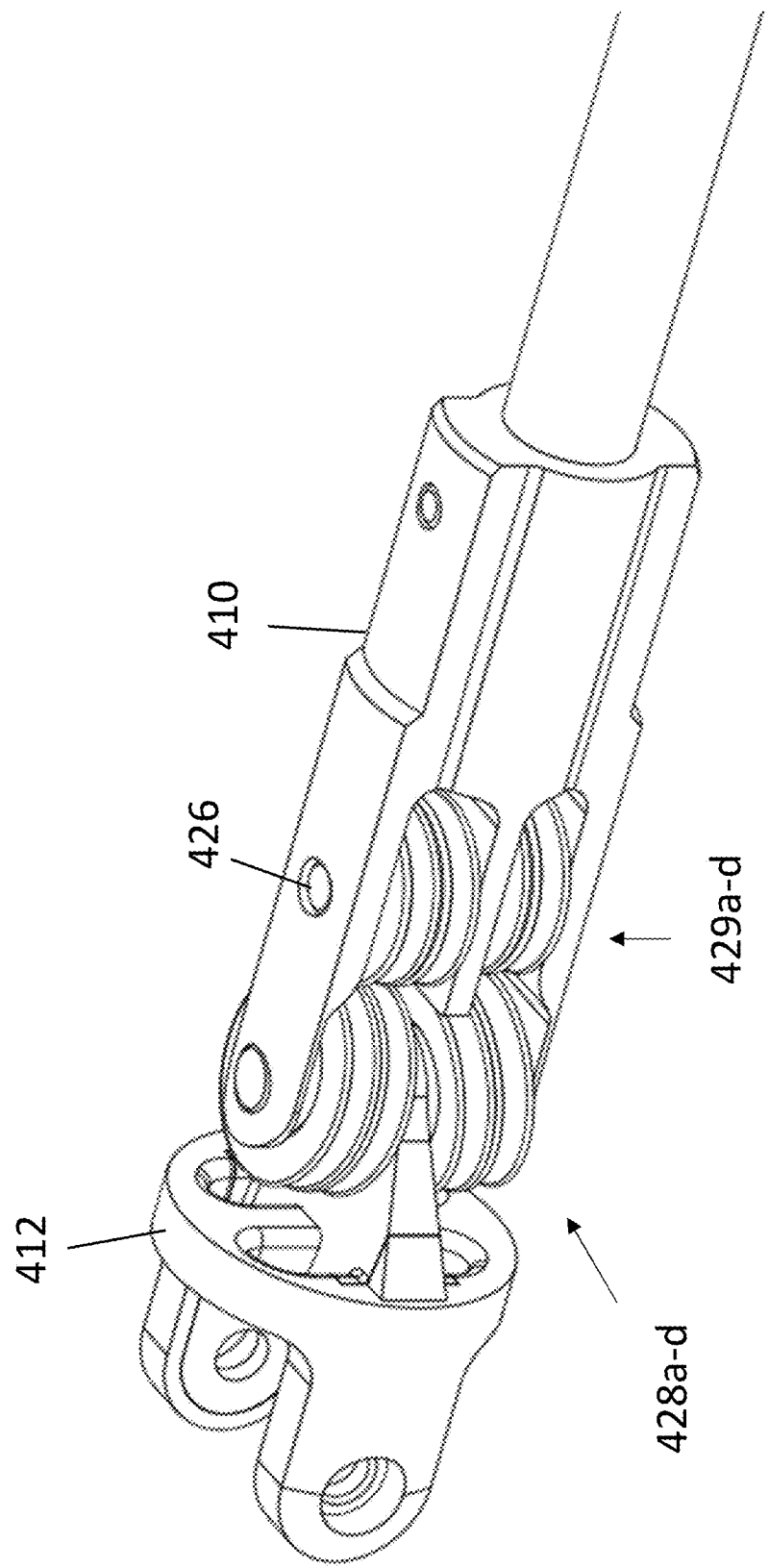
FIG. 25 is similar to FIG. 24A, but also shows the pulleys.

A "fleet angle" is an angle between the cable and the plane that the corresponding pulley is rotating on. Referring to FIG. 26, each cable has a relatively large fleet angle F as it transitions from a jaw member to one of the distal pulleys 428a-d, deviating from its original plane. Although fleet angle can be avoided using smaller pulleys, larger diameter pulleys have advantages, such as improved efficiency; smaller pulleys may necessitate stronger (and thus more expensive) cables than are needed with relatively larger pulleys. A third embodiment is a modified version of the first or second embodiment, and it includes features designed to minimize the impact of this fleet angle on tendon wear. In this embodiment, each distal pulley 428a-d is angled so that its distal-most edge is positioned laterally further from the longitudinal axis than its proximal-most edge. This may be achieved in a variety of ways. As a first example, the bosses 431 on the distal link 412 (FIG. 18) can be made to be angularly oriented, such that their free ends are more proximal to their base. One example of the use of angled bosses 431a on the distal link 412 is shown in FIG. 24A. Each boss 431a therefore has an axis (the axis of rotation of the pulleys that are mounted to that boss), that angles proximally from its point of intersection with the tab 430a as it extends away from tab 430a. FIG. 25 shows the distal pulleys 428a-d mounted to the angled bosses 431a and thus angled in a proximal direction. The proximal pulleys 429a-d are shown mounted on the pins 426 and maintaining a parallel relationship (parallel to the longitudinal axis of the instrument).

As an alternative to the use of the angled bosses, the angle of the cables at the yaw pulleys could be achieved by opening the tolerance between each yaw pulley 428a-d and its corresponding boss, allowing each of the pulleys 428a-d to tilt on its axis.

Other modifications designed to reduce the angle of the cables may be made in addition to, or as alternatives to, those described in this section. For example, the angle can be reduced by increasing the distance between the axes of the distal pulleys 428a-d and the axes of the proximal pulleys 429a-d, and/or the radius of the pulley portion of each jaw member assembly may be reduced.

While certain embodiments have been described above, it should be understood that these embodiments are presented by way of example, and not limitation. It will be apparent to persons skilled in the relevant art that various changes in form and detail may be made therein without departing from the spirit and scope of the invention. Moreover, features of the different embodiments can be combined in different ways to produce other, different, embodiments. This is especially true in light of technology and terms within the relevant art(s) that may be later developed. Moreover, features of the various disclosed embodiments may be combined in various ways to produce various additional embodiments.

Any and all patents, patent applications and printed publications referred to above, including for purposes of priority, are incorporated herein by reference.

What is claimed is:

1. A surgical instrument for use with a robotic manipulator, comprising:
    an elongate shaft;
    an end effector assembly comprising
    an end effector member comprising a distal treatment end and a proximal end, and a tendon pass-through;
    a pair of pulley members, a first one of the pulley members defining an annular surface, and a second one of the pulley members having a lateral surface facing the first one of the pulley members, the pulley members assembled with the proximal end of the end effector member captured between them, the annular surface and the lateral face defining a tendon pathway, the tendon pass-through disposed in the tendon pathway;
    a first tendon having a distal loop portion extending through the tendon pass-through and a pair of legs passing proximally from the pass-through, the pair of legs extending in opposite directions around the tendon pathway and proximally through the shaft;
    a clevis coupled to a distal part of the shaft, the clevis including a pair of distally-extending clevis members disposed on opposite sides of the pair of pulley members;
    a pin extending laterally through the clevis members and the pulley members to couple the end effector assembly to the clevis, the end effector assembly pivotable with respect to an axis of the pin in response to variation of tension on at least one leg of the first tendon.

2. The surgical instrument of claim 1, wherein:
    the end effector member is a first end effector member, the pulley members are first pulley members, and the end effector assembly further includes
        a second end effector member comprising a distal treatment end and a proximal end, and a second tendon pass-through;
        a pair of second pulley members, a first one of the second pulley members defining an annular surface, and a second one of the second pulley members having a lateral face facing the first one of the second pulley members, the second pulley members assembled with the proximal end of the second end effector member captured between them, the annular surface and the lateral face of the second pulley members defining a second tendon pathway, the second tendon pass-through disposed in the second tendon pathway;
    the instrument further includes a second tendon having a distal loop portion extending through the second tendon pass-through and a pair of legs passing proximally from the second tendon pass-through, the pair of legs extending in opposite directions around the second tendon pathway and proximally through the shaft;
    the first pulley members and the second pulley members are positioned between the clevis members;
    the pin extends laterally through the clevis members, the first pulley members and the second pulley members to couple the end effector assembly to the clevis, the first end effector member and the pair of first pulley members pivotable with respect to an axis of the pin in response to variation of tension on at least one leg of the first tendon, the second end effector member and the pair of second pulley members pivotable with respect to an axis of the pin in response to variation of tension on at least one leg of the second tendon, and the end effector assembly pivotable with respect to an axis of the pin in response to variation of tension on at least one leg of the first tendon and at least one leg of the second tendon.

3. The surgical instrument of claim 1, wherein at least one of the pulley members has a face facing the other of the pulley members, the face including a recess, and wherein the proximal end of the end effector member is seated in the recess.

4. The surgical instrument of claim 3, wherein the annular surface of the first one of the pulley members is an external surface of an annular rib, and wherein the recess is defined by the annular rib.

5. The surgical instrument of claim 4, further the face further includes a post, wherein the inner surface of the annular rib and an outer surface of the post define the recess and wherein the pin extends through a through-hole in the post.

6. The surgical instrument of claim 5, wherein the proximal end of the end effector member includes a ring and wherein the ring is positioned encircling the post.

7. The surgical instrument of claim 2, wherein the clevis further includes a proximally-extending member coupled to the shaft by a second pin, the first pin and second pin having axis oriented perpendicular to one another, the end effector assembly and clevis pivotable with respect to an axis of the second pin in response to an increase in tension on both legs of the first tendon or both legs of the second tendon.

8. The surgical instrument of claim 7, further including a pair of wire-guide pulleys on a first side of the proximally-extending member and a pair of wire-guide pulleys on a second side of the proximally-extending member, wherein each of the first and second tendons has a first leg extending around a wire-guide pulley on the first side and a second leg extending around a wire-guide pulley on the second side.

9. The surgical instrument of claim 8, wherein the proximally-extending member includes a first boss on the first side and a second boss on the second side, wherein the second pin extends through the bosses and wherein the wire-guide pulleys are rotatable on corresponding ones of the first and second bosses.

10. The surgical instrument of claim 9, wherein each boss is angled away from the proximally-extending member in a proximal direction.

11. The surgical instrument of claim 1, wherein the first tendon is comprised of at least two tendons coupled together.

12. A method of manufacturing a surgical instrument, comprising:
assembling an end effector assembly by
providing an end effector member comprising a distal treatment end and a proximal end, and a tendon pass-through;
positioning the proximal end between a pair of pulley members such that opposed faces of the pulley members define an annular tendon pathway and such that the tendon pass-through is disposed in the tendon pathway;
positioning distally-extending clevis members of a clevis on opposite sides of the pair of pulley members
positioning a pin laterally through the clevis members and the pulley members to couple the end effector assembly to the clevis, such that the end effector assembly is pivotable with respect to an axis of the pin,
passing a first tendon through the tendon pass-through and extending a pair of legs of the tendon proximally from the pass-through and in opposite directions around the tendon pathway;
coupling the clevis to a distal part of the shaft; and
extending the legs of the first tendon through the shaft.

13. The method of claim 12, wherein:
the end effector member is a first end effector member, the pulley members are first pulley members, and assembling the end effector assembly further includes
providing a second end effector member comprising a distal treatment end and a proximal end, and a second tendon pass-through;
positioning the proximal end of the second end effector assembly between a pair of pulley members such that opposed faces of the pulley members define an annular second tendon pathway and such that the second tendon pass-through is disposed in the second tendon pathway;
the step of positioning the pin includes positioning the pin laterally through the clevis members and the first and second pulley members;
the method further includes
passing a second tendon through the second pass-through and extending a pair of legs of the second tendon proximally from the second pass-through and in opposite directions around the second tendon pathway; and
extending the legs of the second tendon through the shaft.

14. The method of claim 12, wherein
the step of providing an end effector member comprises selecting an end effector member from a plurality of end effector member options, each end effector member option in the plurality of end effector member options having a different type or shape of distal treatment end and an identically shaped proximal end; and
the step of positioning the proximal end of the end effector member between opposed faces of the pulley members includes providing the pair of pulley members, wherein the pulley members provided do not vary depending on the end effector option selected.

15. The method of claim 12, wherein the method includes positioning faces of each pulley member opposed to one another, and seating the proximal end of the end effector member in a recess defined between the opposed faces.

16. The method of claim 12, wherein the annular tendon pathway is defined by an annular rib on a face of one of the pulley members and an opposed face of the other of the pulley members.

17. The method of claim 15 wherein the annular tendon pathway is defined by an annular rib on a face of one of the pulley members and an opposed face of the other of the pulley members, and wherein the method includes positioning the proximal end in a recess defined by the annular rib.

18. The method of claim 17, wherein the proximal end of the end effector member includes a ring and wherein the method includes positioning the ring encircling the post.

19. The method of claim 12, wherein the end effector member is formed of an electrically conductive material, and wherein the tendon is an electrically conductive tendon, and wherein the step of positioning the tendon in the pass-through includes creating electrical contact between the tendon and the end effector member only within the pass-through, and electrically insulating the legs of the tendon.

20. The method of claim 19, wherein the step of positioning the tendon comprises providing an electrically insulated tendon, and disturbing electrical insulation of the tendon within the pass-through.

21. The method of claim 19, wherein the step of positioning the tendon comprises positioning the tendon in the pass-through and then electrically insulating the legs of the tendon.

* * * * *